United States Patent [19]

Shepard et al.

[11] Patent Number: 5,093,332

[45] Date of Patent: Mar. 3, 1992

[54] SUBSTITUTED THIENO(2,3-B)(1,4)THIAZINE-6-SULFONAMIDES AS ANTIGLAUCOMA AGENTS

[75] Inventors: Kenneth L. Shepard, North Wales; Cecilia A. Hunt, Plymouth Meeting, both of Pa.

[73] Assignee: Merck & Co., Inc., Rahway, N.J.

[21] Appl. No.: 603,405

[22] Filed: Oct. 1, 1990

[51] Int. Cl.$^5$ ............... A61K 31/54; C07D 513/00
[52] U.S. Cl. ................. 514/224.2; 544/48; 514/224.5
[58] Field of Search .......... 544/48; 514/224.5, 224.2

[56] References Cited

U.S. PATENT DOCUMENTS

| | | | |
|---|---|---|---|
| 4,677,115 | 6/1987 | Baldwin et al. | 514/432 |
| 4,797,413 | 1/1989 | Baldwin et al. | 514/432 |
| 4,820,848 | 4/1989 | Poticello et al. | 549/23 |
| 4,824,968 | 4/1989 | Ponticello et al. | 549/23 |
| 4,863,922 | 9/1989 | Baldwin et al. | 514/232.5 |

OTHER PUBLICATIONS

Paulmier, C., *Tetrahedron Lett.,* 1978, 21, 1797–1800 (I) French Language.

Paulmier, C., *Bull. Soc. Chim. Fr.,* 1980, II, 151–156 (II) French Language.

*Primary Examiner*—Mukund J. Shah
*Assistant Examiner*—Matthew V. Grumbling
*Attorney, Agent, or Firm*—Joseph F. DiPrima; William H. Nicholson

[57] ABSTRACT

Thieno[2,3-b][1,4]thiazine-6-sulfonamides having the structural formula:

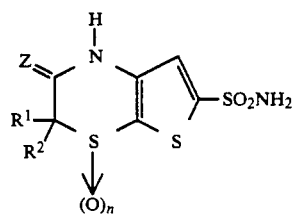

wherein Z, $R^1$, $R^2$, and n are as hereinafter defined, are carbonic anhydrase inhibitors useful in the topical treatment of elevated intraocular pressure and glaucoma.

10 Claims, No Drawings

SUBSTITUTED THIENO(2,3-B)(1,4)THIAZINE-6-SULFONAMIDES AS ANTIGLAUCOMA AGENTS

SUMMARY OF THE INVENTION

This invention relates to novel aromatic sulfonamides useful in the treatment of elevated intraocular pressure. More particularly this invention relates to compounds having the structural formula:

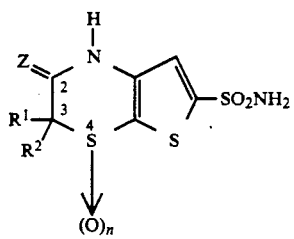

wherein Z, $R^1$, $R^2$, and n are as hereinafter defined, as well as the pharmaceutically and opthalmologically acceptable salts thereof. This invention also relates to pharmaceutical compositions and the use thereof for systemic and ophthalmic use employing a novel compound of this invention as active ingredient for the treatment of elevated intraocular pressure, especially when accompanied by pathological damage such as in the disease known as glaucoma. The invention also relates to processes for preparation of the novel compounds.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2-5-thiadiazol-3-yl)oxyl]-2-propanol, a β-adrenergic blocking agent, was found to reduce intraocular pressure and to be devoid of many unwanted side effects associated with pilocarpine and, in addition, to possess advantages over many other β-adrenergic blocking agents, e.g. to be devoid of local anesthetic properties, to have a long duration of activity, and to display minimal tolerance.

Although pilocarpine, physostigmine and the β-blocking agents mentioned above reduce intraocular pressure, none of these drugs manifests its action by inhibiting the enzyme carbonic anhydrase and, thereby, impending the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in U.S. Pat. Nos. 4,677,115 and 4,797,413. The compounds reported therein are 5,6-dihydrothieno[2,3-b]thiopyran-2-sulfonamides differing from the compounds of the present invention in the nature of the heterocycle fused to the thiophene moiety.

DETAILED DESCRIPTION OF THE INVENTION

The novel compound of this invention has structural formula I:

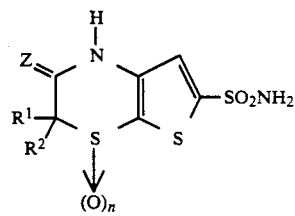

or an ophthalmologically or pharmaceutically acceptable salt thereof, wherein

Z is (H,H), oxo or thioxo;

$R^1$ is (1) hydrogen, or (2) $C_{1-6}$ alkyl;

$R^2$ is (1) hydrogen, or (2) $C_{1-6}$ alkyl, either unsubstituted or substituted with one or more of
(a) $C_{1-3}$ alkoxy,
(b) $C_{1-3}$ alkoxy-$(C_{2-4}$ alkoxy$)_m$-, wherein m is 1-6,
(c) hydroxy,
(d) —$NR^3R^4$ wherein $R^3$ and $R^4$ are independently:
  (i) hydrogen,
  (ii) $C_{1-6}$ alkyl, either unsubstituted or substituted with one or more of hydroxy, $C_{1-3}$ alkoxy, $C_{1-3}$ alkoxy-$(C_{2-4}$ alkoxy$)_m$-, wherein m is as defined above, or;
  (iii) $R^3$ and $R^4$ taken together with the nitrogen atom to which they are attached represent a saturated heterocycle of 5-7 members which may include a second hetero group selected from N, O, S, SO or $SO_2$ such as piperidine, morpholine, piperazine, N—$C_{1-3}$ alkylpiperazine, thiomorpholine, thiomorpholine-S-oxide, or thiomorpholine-S,S-dioxide,
(e) —$CONR^3R^4$, where $R^3$ and $R^4$ are as defined above,
(f) —$CON_3$,
(g) —$CONHNH_2$,
(h) —$CO_2H$, or
(i) —$CO_2R^5$, wherein $R^5$ is $C_{1-6}$ alkyl; and
n is 0, 1 or 2.

In the present invention the compounds may have asymmetric centers and occur as optical isomers. This invention includes all diastereomers, individual enantiomers and mixtures thereof.

When any variable (e.g. alkyl, $R^3$, $R^4$, m, etc.) occurs more than one time in any constituent of formula I, its definition on each occurrence is independent of its definition at every other occurrence. Also, combinations of substituents and/or variables are permissible when such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl, etc.); and "alkoxy" represents an alkyl group of indicated number of carbon atoms attached through an oxygen bridge.

The following additional abbreviations have also been used herein:

| Abbreviated Designation | |
|---|---|
| | Activating Group |
| HOBT | 1-hydroxybenzotriazole hydrate |
| | Condensing Agent |
| CDI | 1,1'-carbonyldiimidazole |
| EDC | 1-(3-dimethylaminopropyl)-3-ethylcarbodiimide hydrochloride |
| | Reagent |
| MCPBA | 3-chloroperoxybenzoic acid |
| TsCl | 4-toluenesulfonyl chloride |
| | Solvent |
| DME | ethylene glycol dimethyl ether |
| DMF | N,N-dimethylformamide |
| THF | tetrahydrofuran |

A preferred embodiment of the novel compound is that wherein

Z is (H,H) or oxo;

$R^1$ is hydrogen;

$R^2$ is $C_{1-6}$ alkyl substituted with one of
  (a) $C_{1-3}$ alkoxy,
  (b) $C_{1-3}$ alkoxy-($C_{2-4}$ alkoxy)-,
  (c) hydroxy,
  (d) —$NR^3R^4$, wherein $R^3$ and $R^4$ are independently selected from
    (i) hydrogen,
    (ii) $C_{1-6}$ alkyl, unsubstituted or substituted with one or more of $C_{1-3}$ alkoxy, or $C_{1-3}$-alkoxy-($C_{2-4}$ alkoxy)-, or
    (iii) $R^3$ and $R^4$ taken together with the nitrogen atom to which they are attached represent a 6-membered saturated heterocycle which may include O such as morpholine,
  (e) —$CONR^3R^4$, wherein $R^3$ and $R^4$ are as defined above,
  (f) —$CON_3$,
  (g) —$CONHNH_2$,
  (h) —$CO_2H$, or
  (i) —$CO_2R^5$, wherein $R^5$ is $C_{1-6}$ alkyl; and n is 0 or 2.

Preferred species of the present invention are the compounds identified as follows:

2,3-dihydro-2-oxo-6-sulfamoyl-1H-thieno[2,3-b][1,4]thiazine;

(2,3-dihydro-2-oxo-6-sulfamoyl-1H-thieno[2,3-b][1,4]thiazin-3-yl)acetic acid;

2,3-dihydro-2,4-dioxo-6-sulfamoyl-1H-thieno-[2,3-b][1,4]thiazine;

2,3-dihydro-6-sulfamoyl-2,4,4-trioxo-1H-thieno[2,3-b][1,4]thiazine;

(2,3-dihydro-2,4,4-trioxo-6-sulfamoyl-1H-thieno[2,3-b][1,4]thiazin-3-yl)acetic acid;

2,3-dihydro-4,4-dioxo-6-sulfamoyl-1H-thieno[2,3-b][1,4]thiazine;

2,3-dihydro-2-thiono-6-sulfamoyl-1H-thieno[2,3-b][1,4]thiazine;

2,3-dihydro-4,4-dioxo-6-sulfamoyl-2-thiono-1H-thieno[2,3-b][1,4]thiazine;

3-(2-hydroxyethyl)-2,3-dihydro-6-sulfamoyl-1H-thieno[2,3-b][1,4]thiazine;

3-(2-hydroxyethyl)-2,3-dihydro-4,4-dioxo-6-sulfamoyl-1H-thieno[2,3-b[]1,4]thiazine;

methyl (2,3-dihydro-2,4,4-trioxo-6-sulfamoyl-1H-thieno[2,3-b][1,4]thiazin-3-yl)acetate;

methyl (2,3-dihydro-2-oxo-6-sulfamoyl-1H-thieno[2,3-b][1,4]thiazine-3-yl)acetate;

(2,3-dihydro-6-sulfamoyl-2,4,4-trioxo-1H-thieno[2,3-b][1,4]thiazin-3-yl)acetic acid hydrazide;

(2,3-dihydro-2,4,4-trioxo-6-sulfamoyl-1H-thieno[2,3-b][1,4]thiazin-3-yl)acetyl azide;

2,3-dihydro-3-ethoxycarbonylaminomethyl-2,4,4-trioxo-6-sulfamoyl-1H-thieno[2,3-b][1,4]thiazine;

N-isobutyl (2,3-dihydro-2-oxo-6-sulfamoyl-1H-thieno[2,3-b][1,4]thiazin-3-yl)acetamide;

N-methoxyethoxyethyl-N-methoxyethyl-(2,3-dihydro-2,4,4-trioxo-6-sulfamoyl-1H-thieno-[2,3-b][1,4]thiazin-3-yl)acetamide;

3-[2-(N-methoxyethoxyethyl-N-methoxyethylamino)ethyl]-2,3-dihydro-2,4,4-trioxo-6-sulfamoyl-1H-thieno[2,3-b][1,4]thiazine;

3-(2-isobutylaminoethyl)-2,3-dihydro-4,4-dioxo-6-sulfamoyl-1H-thieno[2,3-b][1,4]thiazine;

3-[2-bis-(2-methoxyethyl)aminoethyl]-2,3-dihydro-4,4-dioxo-6-sulfamoyl-1H-thieno[2,3-b][1,4]thiazine;

3-[2-(methoxyethoxyethyl-N-methoxyethylamino)ethyl]-2,3-dihydro-4,4-dioxo-6-sulfamoyl-1H-thieno[2,3-b][1,4]thiazine;

3-(2-morpholinoethyl)-2,3-dihydro-4,4-dioxo-6-sulfamoyl-1H-thieno[2,3-b][1,4]thiazine;

or an ophthalmologically or pharmaceutically acceptable salt thereof.

The ophthalmologically acceptable salts of the compounds of this invention include those formed from inorganic acids such as hydrochloric, hydrobromic, sulfuric and phosphoric acids and those formed from organic acids such as maleic acid, fumaric acid, tartaric acid, citric acid, acetic acid, benzoic acid, pyruvic acid, isethionic acid, salicylic acid, succinic acid, lactic acid, methanesulfonic acid, 2-naphthalenesulfonic acid and the like as well as those formed from inorganic bases such as sodium hydroxide, sodium carbonate, sodium bicarbonate, potassium hydroxide, potassium carbonate, ammonium hydroxide and the like.

The novel processes for preparing the novel compounds of the invention are illustrated as follows wherein A is $C_{1-6}$ alkyl, R is H or $C_{1-6}$ alkyl and $R^1$, $R^2$, $R^3$, $R^4$, $R^5$ and n are as defined above unless otherwise indicated.

The first step in the production of the compounds of the present invention is as illustrated below:

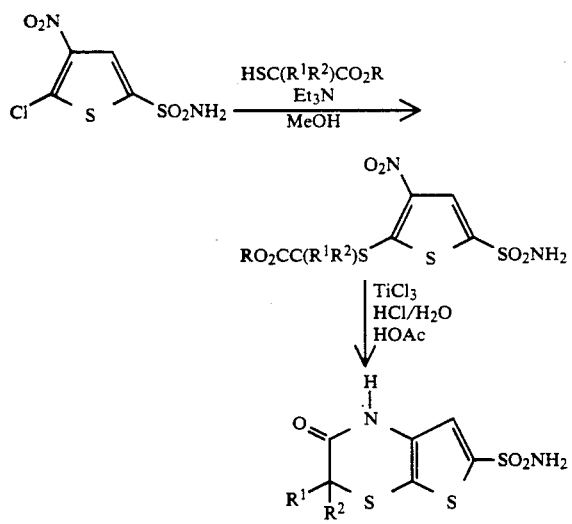

The reaction of 5-chloro-4-nitrothiophene-2-sulfonamide (C. A. Obatemi, *Phosphorous and Sulfur*, 1982, 13, 119) with an appropriately substituted thioacid, thiodiacid or thioglycolate (wherein R is H or $C_{1-6}$ alkyl; $R^1$ is H or $C_{1-6}$ alkyl; and $R^2$ is H, $C_{1-6}$ alkyl or —A—$CO_2H$, wherein A is $C_{1-6}$ alkyl or is absent) in the presence of a base such as pyridine, triethylamine or diisopropylethylamine in a protic solvent such as a $C_{1-6}$ alkanol, preferably ethanol, at or near room temperature for a period of 1 to 24 hours gives the substituted thiothiophene. Reduction of the nitro group with a reagent such as titanium trichloride simultaneously effects cyclization to the thieno[2,3-b][1,4]thiazine ring system.

The sulfide at the 4-position may be oxidized to the sulfoxide or the sulfone by the processes exemplified as follows:

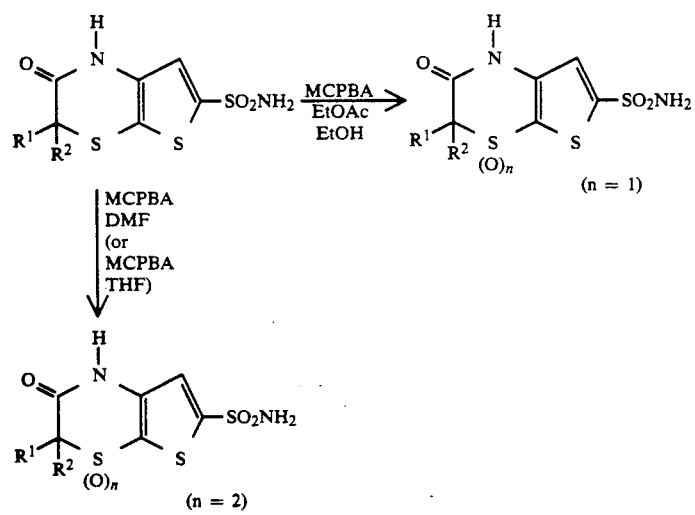

Treatment of the sulfide with approximately 2 equivalents of 3-chloroperoxybenzoic acid in an ethyl acetate/ethanol solution at or near room temperature for 12 to 24 hours gives the corresponding sulfoxide. Similarly, treatment of the sulfide with approximately 3 equivalents of 3-chloroperoxybenzoic acid in a solution of DMF or THF at or near room temperature for 24 to 48 hours gives the corresponding sulfone.

The compounds of the present invention wherein the carbonyl at the 2-position is absent are prepared by reduction which can be exemplified as follows:

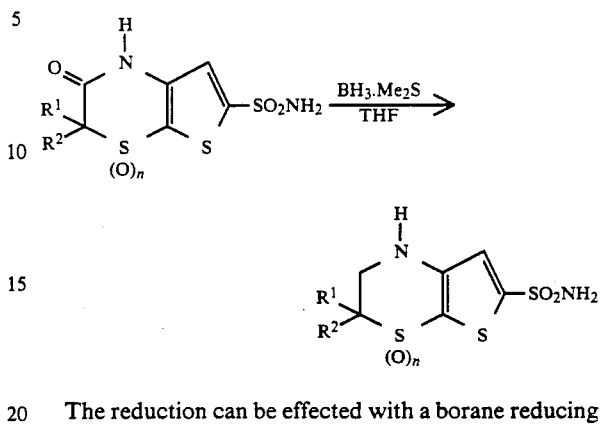

The reduction can be effected with a borane reducing agent such as borane-dimethylsulfide complex, borane-tetrahydrofuran complex, boranepyridine complex, borane-trimethylamine complex or the like, in an etheral solvent such as diethyl ether, THF, 1,2-dimethoxyethane or the like, at about $-10°$ to $+30°$ C. for about 1 to 4 hours. Excess borane is quenched with dilute acid.

The novel compounds of the present invention bearing a thioxo group at the 2-position are prepared from the corresponding lactam as illustrated below:

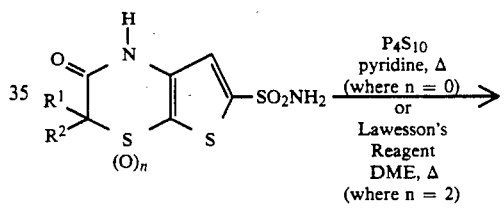

-continued

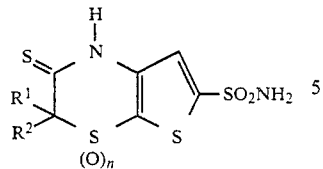

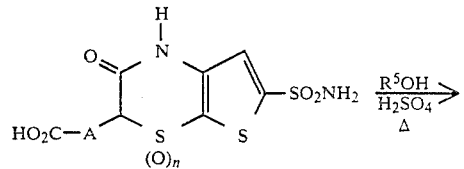

(n = 0-2)

Reaction of the lactam with phosphorous pentasulfide in pyridine at about 50° to 120° C. or alternatively with Lawesson's reagent [2,4-bis(4-methoxyphenyl)-1,3-dithia-2,4-diphosphetane-2,4-disulfide] in DME at about 50° to 90° C. gives the corresponding thione.

The hydroxy compounds of the present invention are prepared by reduction of a carboxylic acid exemplified as follows:

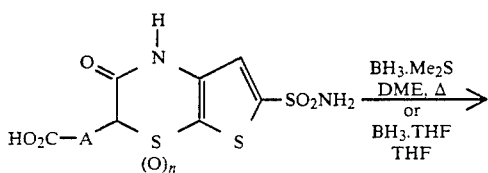

The reaction compromises refluxing a mixture of the carboxylic acid and sulfuric acid in an alcoholic solvent of formula $R^5OH$ for about 4 to 24 hours.

Urethane compounds of the present invention may be prepared from the corresponding carboxylic acid via the corresponding hydrazide and acyl azide as illustrated below:

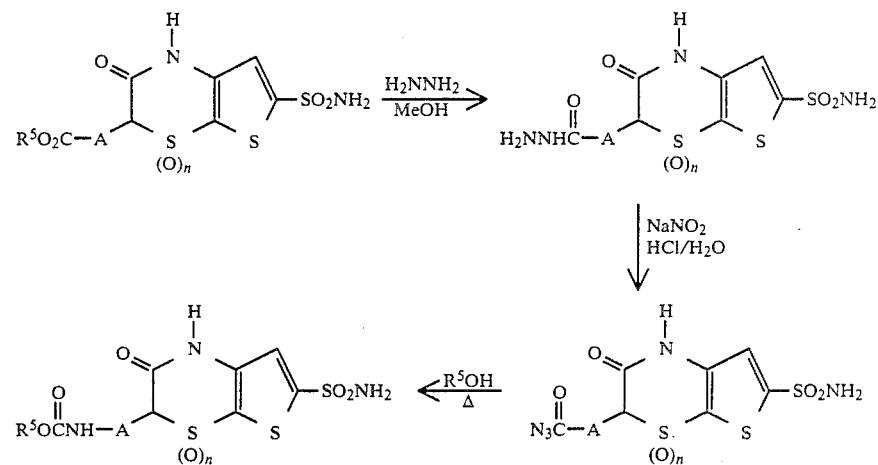

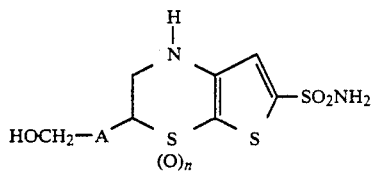

The reduction comprises refluxing a mixture of the carboxylic acid and approximately 5 equivalents of a borane reducing agent such as borane-dimethyl sulfide complex, borane-tetrahydrofuran complex, borane-pyridine complex, borane-trimethylamine complex or the like in DME for about 12 to 36 hours. Excess borane is quenched with methanol.

The novel esters of the present invention may be prepared by esterification of the corresponding carboxylic acid exemplified as follows:

The hydrazides of the present invention are prepared by reacting an appropriate ester with hydrazine in a protic solvent such as $C_{1-6}$ alkanol, preferably methanol or ethanol, at or near room temperature for about 2 to 12 hours. Treatment of a suspension of the hydrazide in aqueous hydrochloric acid with an aqueous solution of sodium nitrite at 0° to 5° C. for 0.25 to 4 hours gives the acyl azide. The urethane compounds of the present invention are then conveniently prepared in a Curtius rearrangement by heating the appropriate acyl azide in an alcoholic solvent of formula $R^5OH$ at or near solvent reflux temperature for about 0.5 to 10 hours.

The amino compounds of the present invention are prepared by peptide-like coupling reactions exemplified as follows:

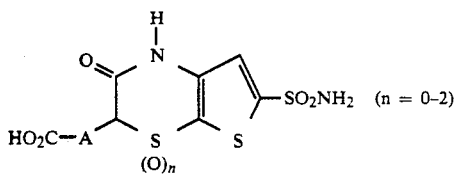

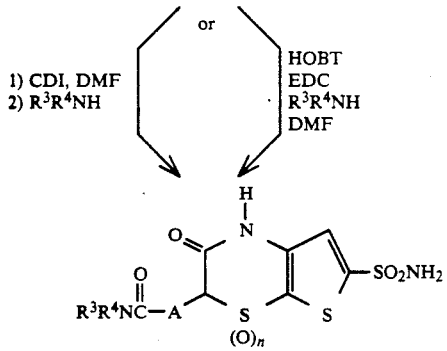

A solution of the carboxylic acid in DMF is reacted with carbonyldiimidazole at or near room temperature for about 1 to 24 hours, followed by the addition of a primary or a secondary amine and further reaction for about 6 to 48 hours. Alternatively, the carboxylic acid is coupled to a primary or a secondary amine with EDC in the presence of HOBT in DMF at or near room temperature for 6 to 48 hours.

One process for preparing substituted amino compounds of the present invention is the reduction of an amide:

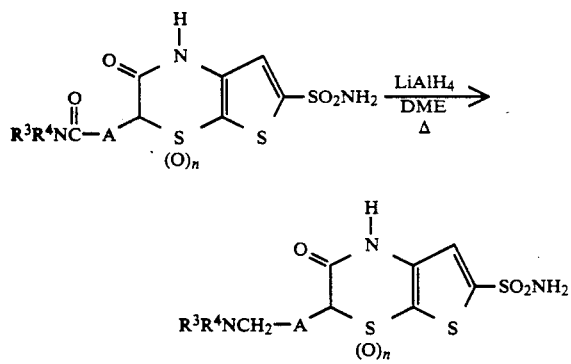

The reduction can be effected with a complex metal hydride such as LiAlH₄ in an ethereal solvent such as 1,2-dimethoxy ethane at or near solvent reflux temperature for about 1 to 6 hours. Excess hydride is quenched with an aqueous solution of Rochelle salt.

Another process for preparing substituted amino compounds is a sequential formation and displacement of a tosylate exemplified as follows:

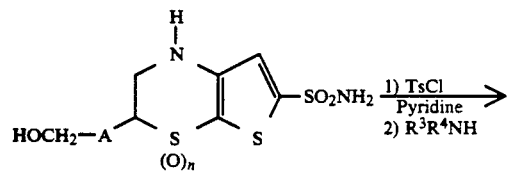

-continued

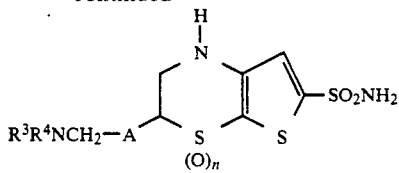

A solution of the alcohol in pyridine is treated with toluenesulfonyl chloride or methanesulfonyl chloride at $-15°$ to $0°$ C. for about 0.25 to 1 hour. The primary or secondary amine or formula $R^3R^4NH$ is added and the reaction mixture is heated at about $80°$ to $115°$ C. for about 6 to 24 hours.

For use in treatment of conditions relieved by the inhibition of carbonic anhydrase, an active compound of the present invention can be administered either systemically, or, in the treatment of the eye, topically.

When given systemically, the drug can be given by any route, although the oral route is preferred. In oral administration, the drug can be employed in any of the usual dosage forms such as tablets or capsules, either in a contemporaneous delivery or sustained release form. Any number of the usual excipients or tableting aids can likewise be included.

When administered for the treatment of glaucoma or other stages of elevated intraocular pressure, the active compound is most desirably administered topically to the eye, although systemic treatment is, as indicated, also possible.

When given by the topical route, the active drug or an ophthalmologically acceptable salt thereof such as the hydrochloride salt is most suitably administered in the form fo ophthalmic pharmaceutical compositions adapted for topical administration to the eye such as a suspension, solution, ointment, solid insert or a solution that gels at body temperature or in the presence of lachrymal fluids. Formulations of these compounds may contain from 0.01 to 15% by weight and especially 0.5% to 2% by weight of medicament, the remainder being comprised of carriers and other excipients well known in the art. Higher dosages as, for example, about 10% by weight, or lower dosages can be employed provided the dose is effective in reducing or controlling elevated intraocular pressure.

The medicament in the novel topical ocular formulations comprise one of the novel compounds of this invention either alone or in combination with a $\beta$-adrenergic blocking agent such as timolol maleate or a parasympathomimetic agent such as pilocarpine or an angiotensin converting enzyme (ACE) inhibitor such as enalaprilat. In such combinations each of the active agents is present in an amount approximating that found in its single entity formulations.

The novel method of treatment of this invention comprises the treatment of elevated intraocular pressure by the administration of a novel compound of this invention or pharmaceutical formulation thereof. Of primary concern is the treatment by topical ocular administration of about 0.01 to 25 mg, preferably 0.05 to 20 mg, and especially 0.1 to 10 mg of such compound, generally on a daily basis in single or on a 2 to 4 dose per day regimen so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The following examples provide, by way of illustration, adequate means for preparation of the novel compounds of the present invention. Alternative processes and process steps should be apparent from this description to those of ordinary skill in the art.

EXAMPLE 1

Preparation of 2,3-Dihydro-2-oxo-6-sulfamoyl-1H-thieno[2,3-b][1,4]thiazine

Step A: Preparation of Methyl (3-Nitro-5-sulfamoylthien-2-yl)thioacetic acid

Triethylamine (3.06 ml, 2.22 g, 22 mmol) was added to a stirred mixture of methyl thioglycolate (2.12 g, 20 mmol) and 5-chloro-4-nitrothiophene-2-sulfonamide (4.90 g, 30 mmol) (C. A. Obatemi, *Phosphorous and Sulfur*, 1982, 13, 119) in methanol (30 ml). After a slight exotherm the reaction mixture became very thick and difficult to stir. The mixture was stirred for an additional 16 hours, then added to water (250 ml). The yellowish solid was collected, washed with water air-dried to yield 5.2 g, mp 153°–154° C. Recrystallization from dichloroethane gave methyl (3-nitro-5-sulfamoylthien-2-yl)thioacetic acid with mp 154°–155° C.

Anal., Calc'd. for $C_7H_8N_2O_6S_3$: C, 26.91; H, 2.58; N, 8.97; Found: C, 26.99; H, 2.49; N, 8.99.

Step B: Preparation of 2,3-Dihydro-2-oxo-6-sulfamoyl-1H-thieno[2,3-b][1,4]thiazine A solution of titanium trichloride (200 ml, 15 wt % in 20–30 wt % hydrochloric acid, 1.16M, 240 mmol) was added in a steady stream to a stirred suspension of methyl (3-nitro-5-sulfamoylthien-2-yl)thioacetic acid (12.5 g, 40 mmol) in 50% aqueous acetic acid (250 ml). A dark purple solution resulted after approximately two hours, and the reaction was allowed to stir overnight. The pale yellow solid that had precipitated was collected, rinsed with cold water and air-dried to yield 7.1 g, mp 243°–245° C. Recrystallization from ethanol gave pure 2,3-dihydro-2-oxo-6-sulfamoyl-1H-thieno[2,3-b][1,4]thiazine.

Anal., Calc'd. for $C_6H_6N_2O_3S_3$: C, 28.79; H, 2.42; N, 11.19; Found: C, 28.90; H, 2.50; N, 11.15.

EXAMPLE 2

Preparation of (2,3-Dihydro-2-oxo-6-sulfamoyl-1H-thieno[2,3-b][1,4]thiazin-3-yl)acetic Acid Step A: Preparation of 5-(2,3-Dicarboxypropylthio)-4-nitrothiophene-2-sulfonamide Triethylamine (81.2 ml, 58.8 g) was added in a steady stream to a stirred solution of mercaptosuccinic acid (50 g) and 5-chloro-4-nitrothiophene-2-sulfonamide (29.4 g) in methanol (1 liter). After a slight initial exotherm, the reaction was stirred at ambient temperature for eighteen hours. The reaction mixture was evaporated to dryness and the residue was dissolved in dilute sodium carbonate solution (750 ml, 5%). The alkaline solution was extracted with ethyl acetate and these extracts were discarded. The aqueous layer was acidified with conc. hydrochloric acid to pH 2 and extracted with ethyl acetate (4×200 ml). The extracts were washed with water, saturated sodium chloride solution and dried over anhydrous sodium sulfate. Filtration and evaporation of the solvent gave 5-(2,3-dicarboxypropylthio)-4-nitrothiophene-2-sulfonamide as a pale yellow solid that was used directly in the next step.

Step B: Preparation of 3-Carboxymethyl-2,3-dihydro-2-oxo-6-sulfamoyl-1H-thieno-[2,3-b][1,4]thiazine Titanium trichloride (256 ml, 15 wt % in 20–30 wt % HCl) was added in a steady stream to a stirred suspension of 5-(2,3-dicarboxypropylthio)-4-nitrothiophene-2-sulfonamide (21.8 g, 61.0 mmol) in water (128 ml) and acetic acid (128 ml). This mixture was stirred at ambient temperature for 18 hours and the yellow solid that precipitated was collected by filtration, washed with water and dried to yield 17.6 g. Chromatography over silica gel using chloroform/methanol/conc. aqueous ammonia (60:30:10; v/v/v) followed by recrystallization from water gave 3-carboxymethyl-2,3-dihydro-2-oxo-6-sulfamoyl-1H-thieno-[2,3-b][1,4]thiazine, mp 240° C.

Anal., Calc'd. for $C_8H_8N_2O_5S_3$: C, 31.16; H, 2.61; N, 9.09; Found: C, 31.40; H, 2.53; N, 9.11.

EXAMPLE 3

Preparation of 2,3-Dihydro-2,4-dioxo-6-sulfamoyl-1H-thieno[2,3-b][1,4]thiazine

To a mixture of 2,3-dihydro-2-oxo-6-sulfamoyl-1H-thieno[2,3-b][1,4]thiazine (0.25 g, 1 mmol) in ethyl acetate (8 ml) and ethanol (8 ml) was added 3-chloroperoxybenzoic acid (0.43 g, 80–85% pure, 2 mmol). The reaction mixture was stirred overnight and the resulting solid collected, triturated with hot ethyl acetate and dried to give 0.25 g, 2,3-dihydro-2,4-dioxo-6-sulfamoyl-1H-thieno[2,3-b][1,4]thiazine, mp 222°–223° C.

Anal., Calc'd. for $C_6H_6N_2O_4S_3$: C, 27.06; H, 2.27; N, 10.52; Found: C, 27.12; H, 2.19; N, 10.38.

EXAMPLE 4

Preparation of 2,3-Dihydro-6-sulfamoyl-2,4,4-trioxo-1H-thieno[2,3-b][1,4]thiazine 3-Chloroperoxybenzoic acid (16 g, 74 mmol) was added to a solution of 2,3-dihydro-2-oxo-6-sulfamoyl-1H-thieno[2,3-b][1,4]thiazine (5.4 g, 21.6 mmol) in freshly degassed DMF (100 ml). The resulting pale yellow solution generated a slight exotherm and was allowed to stir with no external control of the temperature for two hours. A tlc probe (fluorescent silica, chloroform, methanol, acetic acid (90:8:2)) indicated complete conversion of starting material to a new product at a Rf between the initial sulfide and the sulfoxide above. After removal of the DMF under reduced pressure, the residue was recrystallized from water to give 3.85 g 2,3-dihydro-6-sulfamoyl-2,4,4-trioxo-1H-thieno[2,3-b][1,4]thiazine, mp, 259°–260° C.

Anal., Calc'd. for $C_6H_6N_2O_5S_3$: C, 25.52; H, 2.14; N, 9.92; Found: C, 25.56; H, 2.35; N, 9.87.

EXAMPLE 5

Preparation of
(2,3-Dihydro-2,4,4-trioxo-6-sulfamoyl-1H-thieno[2,3-b][1,4]thiazin-3-yl)acetic acid 3-Chloroperoxybenzoic acid (30 g, 80–85% pure) was added to a stirred solution of (2,3-dihydro-2-oxo-6-sulfamoyl-1H-thieno-[2,3-b][1,4]thiazin-3-yl)acetic acid (12.3 g, 39.9 mmol) in freshly degassed DMF (200 ml) at 10°–20° C. The reaction mixture was stirred at ambient temperature for 24 hours and the solvent was removed under vacuum. The residue was treated with methylene chloride and the resulting solid was collected and air-dried to yield 12 g. Recrystallization from water followed by treatment of the solid with hot ethyl acetate gave pure (2,3-dihydro-2,4,4-trioxo-6-sulfamoyl-1H-thieno[2,3-b][1,4]thiazin-3-yl)acetic acid Anal., Calc'd. for $C_8H_8N_2O_7S_3$: C, 28.23; H, 2.37; N, 8.23; Found: C, 28.18; H, 2.31; N, 8.21.

EXAMPLE 6

Preparation of
2,3-Dihydro-4,4-dioxo-6-sulfamoyl-1H-thieno[2,3-b][1,4]thiazine

Borane dimethylsulfide in THF (4.4 ml, 10M, 44 mmol) was added slowly to a solution of 2,3-dihydro-2,4,4-trioxo-6-sulfamoyl-1H-thieno[2,3-b][1,4]thiazine (2.5 g, 8.9 mmol) in THF (10 ml) at 0° C. The reaction mixture was warmed to ambient temperature and stirred for an addidition hour. Excess borane was destroyed by the addition of 6N HCl and borane adducts were cleaved by heating at reflux for one hr. The solvent was removed and the residue was partitioned between water and ethyl acetate. The organic phase was washed with water and brine then dried over sodium sulfate. After filtration and evaporation of the solvent, the residue was chromatographed over silica gel with $CHCl_3/MeOH/NH_4OH$ (80:20:2). Fractions containing the desired product were combined, evaporated and the solid residue was triturated with ethyl acetate to yield 0.36 g 2,3-dihydro-4,4-dioxo-6-sulfamoyl-1H-thieno[2,3-b][1,4]thiazine, mp 250°–252° C.

Anal., Calc'd. for $C_6H_8N_2O_4S_3$: C, 26.85; H, 3.00; N, 10.44; Found: C, 26.23; H, 3.31; N, 10.74.

EXAMPLE 7

Preparation of
2,3-Dihydro-2-thiono-6-sulfamoyl-1H-thieno[2,3-b][1,4]thiazine

A mixture of 2,3-dihydro-2-oxo-6-sulfamoyl-1H-thieno[2,3-b][1,4]thiazine (6.25 g, 25 mmol) and phosphorus pentasulfide (5.55 g, 25 mmol) in pyridine (75 ml) was heated under reflux for one hour. The solvent was removed under reduced pressure and the residue was treated with cold 10% NaOH solution (80 ml). This mixture was stirred for 0.5 hour while maintaining the temperature less than 10° C. The mixture was filtered and the filtrate was treated with cold concentrated hydrochloric acid. After aging overnight, the supernatant was decanted and the residue was treated with 300 ml of boiling water. After filtration and cooling there was obtained 0.90 g of yellow powder. Recrystallization from acetonitrile gave pure 2,3-dihydro-2-thiono-6-sulfamoyl-1H-thieno[2,3-b][1,4]thiazine.

Anal., Calc'd. for $C_6H_6N_2O_2S_4$: C, 27.05; H, 2.27; N, 10.52; Found: C, 26.94; H, 2.14; N, 10.26.

EXAMPLE 8

Preparation of
2,3-Dihydro-4,4-dioxo-6-sulfamoyl-2-thiono-1H-thieno[2,3-b][1,4]thiazine A mixture of 2,3-dihydro-2,4,4-trioxo-6-sulfamoyl-1H-thieno[2,3-b][1,4]thiazine (5 g) and Lawesson's reagent (3.8 g) in dimethoxyethane (25 ml) was heated under reflux for seven hours. The solvent was removed under reduced pressure and the residue was chromatographed over silica gel with chloroform/methanol/acetic acid (90:8:2, v/v/v) as the eluent. The fractions containing the desired product were combined and evaporated to dryness to yield 1.4 g. Two recrystallizations from ethyl acetate/hexane gave pure 2,3-dihydro-4,4-dioxo-6-sulfamoyl-2-thiono-1H-thieno[2,3-b][1,4]thiazine, mp 219°–221° C.

Anal., Calc'd. for $C_6H_6N_2O_4S_4$: C, 24.15; H, 2.03; N, 9.39; Found: C, 24.59; H, 1.73; N, 9.16.

EXAMPLE 9

Preparation of
3-(2-Hydroxyethyl)-2,3-dihydro-6-sulfamoyl-1H-thieno[2,3-b][1,4]thiazine A solution of borane/THF (200 ml, 1M, 200 mmol) was added gradually to a solution of (2,3-dihydro-2-oxo-6-sulfamoyl-1H-thieno-[2,3-b]-[1,4]thiazin-3-yl)acetic acid (12.3 g, 40 mmol) in THF (200 ml). The mixture was stirred at ambient temperature until gas evolution ceased and the resulting clear solution was heated under reflux overnight. The reaction mixture was cooled to 25° C. and treated with methanol (200 ml). When gas evolution ceased, the mixture was evaporated to dryness under vacuum and the residue was restripped from methanol two additional times (2×50 ml). Recrystallization of the residue from water gave 6.4 g 3-(2-hydroxyethyl)-2,3-dihydro-6-sulfamoyl-1H-thieno[2,3-b][1,4]thiazine, mp 145°–147° C. An additional 1.2 g of product was isolated from the filtrate on standing. Further recrystallization from water gave material of mp 149°–150° C.

Anal., Calc'd. for $C_8H_{12}N_2O_3S_3$: C, 34.26; H, 4.32; N, 9.99; Found: C, 33.99; H, 4.23; N, 9.97.

EXAMPLE 10

Preparation of
3-(2-Hydroxyethyl)-2,3-dihydro-4,4-dioxo-6-sulfamoyl-1H-thieno[2,3-b][1,4]thiazine Borane-dimethylsulfide (9.5 ml, 10M, 95 mmol) was added to a solution of (2,3-dihydro-2,4,4-trioxo-6-sulfamoyl-1H-thieno-[2,3-b][1,4]thiazin-3-yl)acetic acid (3.25 g, 9.5 mmol) in dimethoxyethane (325 ml) and the resulting solution was heated under reflux for 24 hours. Methanol (100 ml) was added to the cooled reaction mixture, and after stirring for an additional 24 hours, the mixture was evaporated to a thick oil. The oil was partitioned between water and ethyl acetate and the organic layer was washed with brine and dried over sodium sulfate. Removal of the solvent and recrystallization of the residue from water gave 1.5 g. Chromatographic purification over silica gel eluting with $CHCl_3/MeOH/NH_4OH$ (70:30:3) gave 3-(2-hydroxyethyl)-2,3-dihydro-4,4-dioxo-6-sulfamoyl-1H-thieno[2,3-b][1,4]thiazine, mp 158°–160° C.

Anal., Calc'd. for $C_8H_{12}N_2O_5S_3$: C, 30.76; H, 3.87; N, 8.97; Found: C, 30.55; H, 3.76; N, 9.00.

EXAMPLE 11

Preparation of Methyl (2,3-Dihydro-2,4,4-trioxo-6-sulfamoyl-1H-thieno[2,3-b][1,4]thiazin-3-yl)acetate A mixture of (2,3-dihydro-2,4,4-trioxo-6-sulfamoyl-1H-thieno-[2,3-b][1,4]thiazin-3-yl)acetic acid (5 g) and concentrated sulfuric acid (3 ml) in methanol (50 ml) was heated to reflux for 5 hours. The solvent was removed and the residue was treated with ice cold water. The resulting solid was collected, rinsed with additional cold water and dried at 50° C. to yield 4.05 g. Recrystallization from water gave methyl (2,3-dihydro-2,4,4-trioxo-6-sulfamoyl-1H-thieno-[2,3-b][1,4]thiazin-3-yl)acetate, mp 223°–225° C.

Anal., Calc'd. for $C_9H_{10}N_2O_7S_3$: C, 30.50; H, 2.84; N, 7.91; Found: C, 30.50; H, 2.52; N, 7.99.

EXAMPLE 12

Preparation of Methyl (2,3-Dihydro-2-oxo-6-sulfamoyl-1H-thieno[2,3-b][1,4]thiazin-3-yl)acetate The procedure of Example 11 was followed substituting (2,3-dihydro-2-oxo-6-sulfamoyl-1H-thieno[2,3-b][1,4]thiazin-3-yl)acetic acid as the starting material to give the title compound, mp 195°–197° C.

Anal., Calc'd. for $C_9H_{10}N_2O_5S_3$: C, 33.53; H, 3.13; N, 8.69; Found: C, 33.22; H, 3.01; N, 8.55.

EXAMPLE 13

Preparation of (2,3-Dihydro-6-sulfamoyl-2,4,4-trioxo-1H-thieno[2,3-b][1,4]thiazin-3-yl)acetic Acid Hydrazide Anhydrous hydrazine (1 ml) was added to a solution of methyl (2,3-dihydro-2,4,4-trioxo-6-sulfamoyl-1H-thieno[2,3-b][1,4]thiazin-3-yl)acetate (1.0 g) in methanol (10 ml) at ambient temperature with stirring. After 5–6 hours, the methanol was removed under reduced pressure and the residue was treated with water (10 ml). The pH was adjusted to 6.5 and the resulting precipitate was collected, rinsed with water and dried under vacuum to give 0.40 g (2,3-dihydro-6-sulfamoyl-2,4,4-trioxo-1H-thieno[2,3-b][1,4]thiazin-3-yl)acetic acid hydrazide, mp 230° C., dec.

Anal., Calc'd. for $C_8H_{10}N_4O_6S_3$: C, 27.11; H, 2.85; N, 15.81; Found: C, 26.92; H, 2.85; N, 15.84.

EXAMPLE 14

Preparation of 2,3-Dihydro-3-ethoxycarbonylaminomethyl-2,4,4-trioxo-6-sulfamoyl-1H-thieno[2,3-b][1,4]thiazine Step A: Preparation of (2,3-Dihydro-2,4,4-trioxo-6-sulfamoyl-1H-thieno[2,3-b][1,4]thiazin-3-yl)acetyl azide A solution of sodium nitrite (0.34 g, 5 mmol) in water (10 ml) was added slowly to a cold (0°–5° C. suspension of (2,3-dihydro-6-sulfamoyl-2,4,4-trioxo-1H-thieno[2,3-b][1,4]thiazin-3-yl)acetic acid hydrazide (1.75 g, 5 mmol) in 1N HCl (150 ml). The reaction mixture was stirred for 0.5 hours in the cold and the resulting solid was collected, rinsed with water and air-dried to yield 1.05 g (2,3-dihydro-2,4,4-trioxo-6-sulfamoyl-1H-thieno-[2,3-b][1,4]thiazin-3-yl)acetyl azide.

Step B: Preparation of 2,3-Dihydro-3-ethoxycarbonylaminomethyl-2,4,4-trioxo-6-sulfamoyl-1H-thieno[2,3-b][1,4]thiazine A mixture of (2,3-dihydro-2,4,4-trioxo-6-sulfamoyl-1H-thieno[2,3-b][1,4]thiazin-3-yl)acetyl azide (1.05 g) and ethanol 20 ml was heated under reflux for 1.5 hours. The cooled reaction mixture was filtered and the collected solid was recrystallized from acetonitrile to yield 2,3-dihydro-3-ethoxycarbonylaminomethyl-2,4,4-trioxo-6-sulfamoyl-1H-thieno[2,3-b][1,4]thiazine.

Anal., Calc'd. for $C_{10}H_{13}N_3O_7S_3$: C, 31.32; H, 3.42; N, 10.96; Found: C, 31.54; H, 3.21; N, 11.00.

EXAMPLE 15

Preparation of N-Isobutyl (2,3-Dihydro-2-oxo-6-sulfamoyl-1H-thieno[2,3-b][1,4]thiazin-3-yl)acetamide 1,1-Carbonyldiimidazole (3.2 g, 19 mmol) was added to a solution of (2,3-dihydro-2-oxo-6-sulfamoyl-1H-thieno-[2,3-b][1,4]thiazin-3-yl)acetic acid (5 g, 16 mmol) in dry DMF (65 ml) and the resulting solution was stirred at ambient temperature for 5 hours. Isobutyl amine (1.9 ml) was added and stirring was continued for an additional 18 hours. The solvent was removed under vacuum and the residue was triturated with 0.5N HCl to give 5.83 g of brown solid. The crude product was chromatographed over silica gel eluting with CHCl$_3$/MeOH/NH$_4$OH (90:10:1). Appropriate fractions containing the desired product were evaporated and the residue was recrystallized from methanol to give N-isobutyl (2,3-dihydro-2-oxo-6-sulfamoyl-1H-thieno[2,3-b][1,4]thiazin-3-yl)acetamide, mp >250° C.

Anal., Calc'd. for $C_{12}H_{17}N_3O_4S_3$: C, 39.65; H, 4.72; N, 11.56; Found: C, 39.74; H, 4.45; N, 11.51.

EXAMPLE 16

Preparation of N-Methoxyethoxyethyl-N-methoxyethyl(2,3-dihydro-2,4,4-trioxo-6-sulfamoyl-1H-thieno[2,3-b][1,4]thiazin-3-yl)acetamide To a solution of (2,3-dihydro-2,4,4-trioxo-6-sulfamoyl-1H-thieno[2,3-b][1,4]thiazin-3-yl)acetic acid (3 g, 9 mmol) in dry DMF (25 ml) was added hydroxybenzotriazole hydrate (1.22 g, 9 mmol), N-methoxyethoxyethyl-N-methoxyethylamine (3.19 g, 18 mmol) and 1-ethyl-3-(3-dimethylaminopropyl)carbodiimide hydrochloride (2.59 g, 14 mmol), and the resulting reaction mixture was stirred overnight. Water (10 ml) was added, the mixture stirred an additional 2 hours and concentrated to dryness under reduced pressure. The residue was treated with 0.5N HCl and the pH adjusted to 6.5–6.9 by the additon of dilute NH$_4$OH. The aqueous mixture was extracted with ethyl acetate and the combined extracts were washed with brine and dried over sodium sulfate. After filtration and removal of the solvent, the residue was recrystallized from water to give N-methoxyethoxyethyl-N-methoxyethyl-(2,3-dihydro-2,4,4-trioxo-6-sulfamoyl-1H-thieno-[2,3-b][1,4]thiazin-3-yl)acetamide, mp 156°–158° C.

Anal., Calc'd. for $C_{16}H_{25}N_3O_9S_3$: C, 38.46; H, 5.04; N, 8.41; Found: C, 38.22; H, 4.86; N, 8.36.

EXAMPLE 17

Preparation of
3-[2-(N-Methoxyethoxyethyl-N-methoxyethylamino)ethyl]-2,3-dihydro-2,4,4-trioxo-6-sulfamoyl-1H-thieno[2,3-b][1,4]thiazine A solution of N-methoxyethoxyethyl-N-methoxyethyl (2,3-dihydro-2,4,4-trioxo-6-sulfamoyl-1H-thieno[2,3-b][1,4]thiazin-3-yl)acetamide (500 mg, 1 mmol) in dimethoxyethane (5 ml) was added dropwise to a suspension of lithium aluminum hydride (152 mg, 4 mmol) in dimethoxyethane (5 ml) at such a rate that the mixture refluxed gently. When addition was complete, the reaction mixture was refluxed an additional 2 hours. The mixture was cooled in an ice bath and a saturated solution of Rochelle salt was added. The resulting mixture was stirred overnight at ambient temperature, filtered to remove some granular solid, and concentrated to dryness under vacuum. The residue was partitioned between ethyl acetate and 0.5N HCl. The acid fraction was brought to pH 8 by the addition of NH$_4$OH and extracted with ethyl acetate. This ethyl acetate extract was washed with brine and dried over sodium sulfate. After filtration and evaporation of solvent the residue was chromatographed over silica gel eluting with CHCl$_3$/MeOH/NH$_4$OH (70:30:3) to give 3-[2-(N-methoxyethoxyethyl-N-methoxyethylamino)ethyl]-2,3-dihydro-2,4,4-trioxo-6-sulfamoyl-1H-thieno[2,3-b][1,4]thiazine. The free base was converted to the hydrochloride salt hydrate from ethanolic hydrogen chloride and ether, mp 170°-175° C.

Anal., Calc'd. for C$_{16}$H$_{27}$N$_3$O$_8$S$_3$•HCl•H$_2$O: C, 36.81; H, 5.41; N, 8.05; Found: C, 36.53; H, 5.75; N, 7.99.

EXAMPLE 18

Preparation of
3-(2-Isobutylaminoethyl)-2,3-dihydro-4,4-dioxo-6-sulfamoyl-1H-thieno[2,3-b][1,4]thiazine Hydrochloride Toluenesulfonyl chloride (1.91 g, 10 mmol) was added portionwise over 50 minutes to a cold (−10° C. to −5° C.) solution of 3-(2-hydroxyethyl)-2,3-dihydro-4,4-dioxo-6-sulfamoyl-1H-thieno[2,3-b][1,4]thiazine (1.56 g, 5 mmol) in pyridine (10 ml). This solution was stirred for about 0.5 hr as the temperature rose to 0° C., then isobutylamine (10 ml) was added. The resulting solution was heated at 100° C. overnight. The reaction mixture was concentrated to dryness, and the residue was treated with chloroform. The resulting white solid, 1.7 g, was dissolved in a minimum amount of water, the pH was adjusted to 7.5 and the solution was extracted with ethyl acetate. The organic layer was washed with brine and dried over sodium sulfate. After removal of the dried solvent, the residue was dissolved in ethanol and treated with excess ethanolic hydrogen chloride. Ether was added to the cloud point and the mixture aged for 18 hours. The resulting solid was collected and dried to yield 1.2 g 3-(2-isobutylaminoethyl)-2,3-dihydro-4,4-dioxo-6-sulfamoyl-1H-thieno[2,3-b][1,4]thiazine hydrochloride, mp 263°-265° C.

Anal., Calc'd. for C$_{12}$H$_{21}$N$_3$O$_4$S$_3$•HCl: C, 35.68; H, 5.49; N, 10.40; Found: C, 35.30; H, 5.42; N, 10.38.

EXAMPLE 19

Preparation of
3-[2-Bis-(2-methoxyethyl)aminoethyl]-2,3-dihydro-4,4-dioxo-6-sulfamoyl-1H-thieno[2,3-b][1,4]thiazine Hydrochloride The procedure of Example 18 was followed replacing isobutylamine with bis-(2-methoxyethyl)amine to give 3-[2-bis-(2-methoxyethyl)aminoethyl]-2,3-dihydro-4,4-dioxo-6-sulfamoyl-1H-thieno[2,3-b][1,4]thiazine hydrochloride, mp 140°-142° C.

Anal., Calc'd. for C$_{14}$H$_{25}$N$_3$O$_6$S$_3$•HCl: C, 36.23; H, 5.65; N, 9.06; Found: C, 36.40; H, 5.72; N, 8.86.

EXAMPLE 20

Preparation of
3-[2-(N-Methoxyethoxyethyl-N-methoxyethylamino)ethyl]-2,3-dihydro-4,4-dioxo-6-sulfamoyl-1H-thieno[2,3-b][1,4]thiazine Hydrochloride The procedure of Example 18 was followed replacing isobutylamine with N-methoxyethoxyethyl-N-methoxyethylamine to give 3-[2-(N-methoxyethoxyethyl-N-methoxyethylamino)ethyl]-2,3-dihydro-4,4-dioxo-6-sulfamoyl-1H-thieno[2,3-b][1,4]thiazine hydrochloride as a hygroscopic solid, mp 75°-100° C.

Anal., Calc'd. for C$_{16}$H$_{29}$N$_3$O$_7$S$_3$•HCl: C, 37.82; H, 5.95; N, 8.27; Found: C, 37.79; H, 5.92; N, 7.94.

EXAMPLE 21

Preparation of
3-(2-Morpholinoethyl)-2,3-dihydro-4,4-dioxo-6-sulfamoyl-1H-thieno[2,3-b][1,4]thiazine Hydrochloride The procedure of Example 18 was followed replacing isobutylamine with morpholine to give 3-(2-morpholinoethyl)-2,3-dihydro-4,4-dioxo-6-sulfamoyl-1H-thieno[2,3-b][1,4]thiazine hydrochloride, mp 280°-282° C.

Anal., Calc'd. for C$_{12}$H$_{19}$N$_3$O$_5$S$_3$•HCl: C, 34.48; H, 4.82; N, 10.05; Found: C, 34.47; H, 4.74; N, 10.04.

EXAMPLE 22

Preparation of
(2,3-Dihydro-3-methyl-2-oxo-6-sulfamoyl-1H-thieno[2,3-b][1,4]thiazin-3-yl)acetic Acid The title compound is prepared by the method of Example 2(A&B) utilizing 2-mercapto-2-methyl-1,4-butanedioic acid as starting material.

EXAMPLES 23-31

Utilizing the general procedures in Examples 1-21, the following compounds of Formula I wherein Z is oxo and n is 2 are prepared from the appropriately substituted starting materials.

TABLE 1

| Compound No. | R$^2$ | R$^1$ |
|---|---|---|
| 23 | —CH$_2$CH$_3$ | —CH$_3$ |
| 24 | —CH$_2$CH$_2$CH$_2$CH$_3$ | —CH$_3$ |
| 25 | —CH$_2$CH$_2$CH$_2$OCH$_2$CH$_3$ | H |
| 26 | —CH$_2$CH$_2$N(CH$_2$CH$_3$)$_2$ | —CH$_3$ |
| 27 | —CH$_2$CH$_2$N[CH$_2$CH(CH$_3$)$_2$]$_2$ | H |
| 28 | —CH$_2$CH$_2$N[CH$_2$CH$_2$OCH$_2$CH$_2$OCH$_3$]$_2$ | H |
| 29 | —CH$_2$CH$_2$C(O)OCH$_2$CH$_3$ | H |
| 30 | —CH$_2$C(O)OCH(CH$_3$)$_2$ | H |
| 31 | —CH$_2$CH$_2$NHC(O)OCH$_3$ | H |

Ophthalmic Formulations

EXAMPLE 32

| | | |
|---|---|---|
| 3-(2-Isobutylaminoethyl)-2,3-dihydro-4,4-dioxo-6-sulfamoyl-1H-thieno[2,3,-b][1,4]thiazine | 1 mg | 15 mg |
| Monobasic sodium phosphate.$2H_2O$ | 9.38 mg | 6.10 mg |
| Dibasic sodium phosphate.$12H_2O$ | 28.48 mg | 16.80 mg |
| Benzalkonium chloride | 0.10 mg | 0.10 mg |
| Water for injection q.s. ad. | 1.0 ml | 1.0 ml |

The active compound, phosphate buffer salts, and benzalkonium chloride are added to and dissolved in water. The pH of the composition is adjusted to 5.4–7.4 and diluted to volume. The composition is rendered sterile by ionizing radiation.

EXAMPLE 33

| | |
|---|---|
| 2,3-Dihydro-6-sulfamoyl-2,4,4-trioxo-1H-thieno[2,3-b]-[1,4]thiazine | 5 mg |
| petrolatum q.s. ad. | 1 gram |

The compound and the petroleum are aseptically combined.

EXAMPLE 34

| | |
|---|---|
| 3-(2-Hydroxyethyl)-2,3-dihydro-4,4-dioxo-6-sulfamoyl-1H-thieno[2,3-b][1,4]thiazine | 1 mg |
| Hydroxypropylcellulose q.s. | 12 mg |

Ophthalmic inserts are manufactured from compression molded films which are prepared on a Carver Press by subjecting the powdered mixture of the above ingredients to a compressional force of 12,000 lbs (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 35

Carbonic Anhydrase Inhibition Assay and Carbonic Anhydrase Binding Assay

The compounds were assayed for in vitro inhibition of human carbonic anhydrase II and in vitro binding for human carbonic anhydrase II essentially as described in *J. Med. Chem.*, 1987, 30, 591.

| Example No. of Product Compound | $IC_{50}$ (M) | $K_i$ (M) |
|---|---|---|
| 1 | $<1 \times 10^{-5}$ | $<1 \times 10^{-5}$ |
| 2 | $<1 \times 10^{-5}$ | $<1 \times 10^{-5}$ |
| 3 | $<1 \times 10^{-5}$ | $<1 \times 10^{-5}$ |
| 4 | $<1 \times 10^{-5}$ | $<1 \times 10^{-5}$ |
| 5 | $<1 \times 10^{-5}$ | $<1 \times 10^{-5}$ |
| 6 | $<1 \times 10^{-5}$ | $<1 \times 10^{-5}$ |
| 8 | $<1 \times 10^{-5}$ | $<1 \times 10^{-5}$ |
| 9 | $<1 \times 10^{-5}$ | $<1 \times 10^{-5}$ |
| 10 | $<1 \times 10^{-5}$ | $<1 \times 10^{-5}$ |
| 11 | $<1 \times 10^{-5}$ | $<1 \times 10^{-5}$ |
| 12 | $<1 \times 10^{-5}$ | $<1 \times 10^{-5}$ |
| 13 | $<1 \times 10^{-5}$ | $<1 \times 10^{-5}$ |
| 14 | $<1 \times 10^{-5}$ | $<1 \times 10^{-5}$ |
| 15 | $<1 \times 10^{-5}$ | $<1 \times 10^{-5}$ |
| 16 | $<1 \times 10^{-5}$ | $<1 \times 10^{-5}$ |
| 17 | $<1 \times 10^{-5}$ | $<1 \times 10^{-5}$ |
| 18 | $<1 \times 10^{-5}$ | $<1 \times 10^{-5}$ |
| 19 | $<1 \times 10^{-5}$ | $<1 \times 10^{-5}$ |
| 20 | $<1 \times 10^{-5}$ | $<1 \times 10^{-5}$ |
| 21 | $<1 \times 10^{-5}$ | $<1 \times 10^{-5}$ |

While the foregoing specification teaches the principles of the present invention, with examples provided for the purpose of illustration, it will be understood that the practice of the invention encompasses all of the casual variations, adaptions, modifications, deletions, or additions of procedures and protocols described herein, as come within the scope of the following claims and its equivalents.

What is claimed is:

1. A compound of the structural formula I:

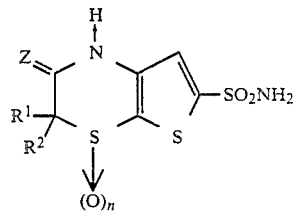

or an ophthalmologically or pharmaceutically acceptable salt thereof, wherein

Z is (H,H), oxo or thioxo;

$R^1$ is (1) hydrogen, or (2) $C_{1-6}$ alkyl;

$R^2$ is (1) hydrogen, or (2) $C_{1-6}$ alkyl; either unsubstituted or substituted with one or more of
 (a) $C_{1-3}$ alkoxy,
 (b) $C_{1-3}$ alkoxy-$(C_{2-4}$alkoxy$)_m$-, wherein m is 1–6,
 (c) hydroxy,
 (d) —$NR^3R^4$ wherein $R^3$ and $R^4$ are independently:
  (i) hydrogen,
  (ii) $C_{1-6}$ alkyl, either unsubstituted or substituted with one or more of hydroxy, $C_{1-3}$ alkoxy, $C_{1-3}$ alkoxy-$(C_{2-4}$ alkoxy$)_m$-, wherein m is as defined above, or;
  (iii) $R^3$ and $R^4$ taken together with the nitrogen atom to which they are attached represent a saturated heterocycle of 5–7 members which may include a second heteroatom selected from N, O, S, SO or $SO_2$ and is selected from piperidine, morpholine, piperazine, N—$C_{1-3}$ alkylpiperazine, thiomorpholine, thiomorpholine-S-oxide, or thiomorpholine-S,S-dioxide,
 (e) —$CONR^3R^4$, where $R^3$ and $R^4$ are as defined above,
 (f) —$CON_3$,
 (g) —$CONHNH_2$,
 (h) —$CO_2H$, or
 (i) —$CO_2R^5$, wherein $R^5$ is $C_{1-6}$ alkyl; and n is 0, 1 or 2.

2. The compound of claim 1, wherein $R^1$ is hydrogen.

3. The compound of claim 2, wherein Z is (H,H) or oxo.

4. The compound of claim 3, wherein $R^2$ is $C_{1-6}$ alkyl substituted with one of (a) $C_{1-3}$ alkoxy,
(b) $C_{1-3}$ alkoxy-($C_{2-4}$ alkoxy)-,
(c) hydroxy,
(d) —$NR^3R^4$, wherein $R^3$ and $R^4$ are independently selected from
  (i) hydrogen,
  (ii) $C_{1-6}$ alkyl, unsubstituted or substituted with one or more of $C_{1-3}$ alkoxy, or $C_{1-3}$-alkoxy-($C_{2-4}$ alkoxy)-, or
  (iii) $R^3$ and $R^4$ taken together with the nitrogen atom to which they are attached represent a 6-membered saturated heterocycle which may include an oxygen heteroatom
(e) —$CONR^3R^4$, wherein $R^3$ and $R^4$ are as defined above,
(f) —$CON_3$,
(g) —$CONHNH_2$,
(h) —$CO_2H$, or
(i) —$CO_2R^5$, wherein $R^5$ is $C_{1-6}$ alkyl.

5. The compound of claim 4, wherein n is 0 or 2.

6. The compound selected from the group of
2,3-dihydro-2-oxo-6-sulfamoyl-1H-thieno[2,3-b][1,4]thiazine;
(2,3-dihydro-2-oxo-6-sulfamoyl-1H-thieno[2,3-b][1,4]thiazine-3-yl)acetic acid;
2,3-dihydro-2,4-dioxo-6-sulfamoyl-1H-thieno[2,3-b][1,4]thiazine;
2,3-dihydro-6-sulfamoyl-2,4,4-trioxo-1H-thieno[2,3-b][1,4]thiazine;
(2,3-dihydro-2,4,4-trioxo-6-sulfamoyl-1H-thieno[2,3-b][1,4]thiazin-3-yl)acetic acid;
2,3-dihydro-4,4-dioxo-6-sulfamoyl-1H-thieno[2,3-b][1,4]thiazine;
2,3-dihydro-2-thiono-6-sulfamoyl-1H-thieno[2,3-b][1,4]thiazine;
2,3-dihydro-4,4-dioxo-6-sulfamoyl-2-thiono-1H-thieno[2,3-b][1,4]thiazine;
3-(2-hydroxyethyl)-2,3-dihydro-6-sulfamoyl-1H-thieno[2,3-b][1,4]thiazine;
3-(2-hydroxyethyl)-2,3-dihydro-4,4-dioxo-6-sulfamoyl-1H-thieno[2,3-b][1,4]thiazine;
methyl (2,3-dihydro-2,4,4-trioxo-6-sulfamoyl-1H-thieno[2,3-b][1,4]thiazin-3-yl)acetate;
methyl (2,3-dihydro-2-oxo-6-sulfamoyl-1H-thieno[2,3-b][1,4]thiazine-3-yl)acetate;
(2,3-dihydro-6-sulfamoyl-2,4,4-trioxo-1H-thieno[2,3-b][1,4]thiazin-3-yl)acetic acid hydrazide;
(2,3-dihydro-2,4,4-trioxo-6-sulfamoyl-1H-thieno[2,3-b][1,4]thiazin-3-yl)acetyl azide;
2,3-dihydro-3-ethoxycarbonylaminomethyl-2,4,4-trioxo-6-sulfamoyl-1H-thieno[2,3-b][1,4]thiazine;
N-isobutyl (2,3-dihydro-2-oxo-6-sulfamoyl-1H-thieno[2,3-b][1,4]thiazin-3-yl)acetamide;
N-methoxyethoxyethyl-N-methoxyethyl-(2,3-dihydro-2,4,4-trioxo-6-sulfamoyl-1H-thieno[2,3-b][1,4]thiazin-3-yl)acetamide;
3-[2-(N-methoxyethoxyethyl-N-methoxyethylamino)ethyl]-2,3-dihydro-2,4,4-trioxo-6-sulfamoyl-1H-thieno[2,3-b][1,4]thiazine;
3-(2-isobutylaminoethyl)-2,3-dihydro-4,4-dioxo-6-sulfamoyl-1H-thieno[2,3-b][1,4]thiazine;
3-[2-bis-(2-methoxyethyl)aminoethyl]-2,3-dihydro-4,4-dioxo-6-sulfamoyl-1H-thieno[2,3-b][1,4]thiazine;
3-[2-(N-methoxyethoxyethyl-N-methoxyethylamino)ethyl]-2,3-dihydro-4,4-dioxo-6-sulfamoyl-1H-thieno[2,3-b][1,4]thiazine;
3-(2-morpholinoethyl)-2,3-dihydro-4,4-dioxo-6-sulfamoyl-1H-thieno[2,3-b][1,4]thiazine;
or an ophthalmologically acceptable salt thereof.

7. An ophthalmological formulation for the treatment of ocular hypertension comprising an ophthalmologically acceptable carrier and an effective ocular antihypertensive amount of the compound of claim 1.

8. The formulation of claim 7 wherein the compound is selected from the group of:
(2,3-dihydro-2-oxo-6-sulfamoyl-1H-thieno[2,3-b][1,4]thiazin-3-yl)acetic acid;
3-(2-hydroxyethyl)-2,3-dihydro-6-sulfamoyl-1H-thieno[2,3-b][1,4]thiazine;
3-(2-hydroxyethyl)-2,3-dihydro-4,4-dioxo-6-sulfamoyl-1H-thieno[2,3-b][1,4]thiazine;
methyl (2,3-dihydro-2,4,4-trioxo-6-sulfamoyl-1H-thieno[2,3-b][1,4]thiazin-3-yl)acetate;
methyl (2,3-dihydro-2-oxo-6-sulfamoyl-1H-thieno[2,3-b][1,4]thiazin-3-yl)acetate;
N-isobutyl (2,3-dihydro-2-oxo-6-sulfamoyl-1H-thieno[2,3-b][1,4]thiazin-3-yl)acetamide;
N-methoxyethoxyethyl-N-methoxyethyl-(2,3-dihydro-2,4,4-trioxo-6-sulfamoyl-1H-thieno[2,3-b][1,4]thiazin-3-yl)acetamide;
3-[2-(N-methoxyethoxyethyl-N-methoxyethylamino)ethyl]-2,3-dihydro-2,4,4-trioxo-6-sulfamoyl-1H-thieno[2,3-b][1,4]thiazine;
3-(2-isobutylaminoethyl)-2,3-dihydro-4,4-dioxo-6-sulfamoyl-1H-thieno[2,3-b][1,4]thiazine;
3-[2-bis-(2-methoxyethyl)aminoethyl]-2,3-dihydro-4,4-dioxo-6-sulfamoyl-1H-thieno[2,3-b][1,4]thiazine;
3-[2-(N-methoxyethoxyethyl-N-methoxyethylamino)ethyl]-2,3-dihydro-4,4-dioxo-6-sulfamoyl-1H-thieno[2,3-b][1,4]thiazine;
3-(2-morpholinoethyl)-2,3-dihydro-4,4-dioxo-6-sulfamoyl-1H-thieno[2,3-b][1,4]thiazine;
or an ophthalmologically acceptable salt thereof.

9. A method of treating ocular hypertension which comprises the topical ocular administration of an effective ocular antihypertensive amount of the compound of claim 1 to a patient in need of such treatment.

10. The method of claim 9 wherein the compound is selected from the group of:
(2,3-dihydro-2-oxo-6-sulfamoyl-1H-thieno[2,3-b][1,4]thiazin-3-yl) acetic acid;
3-(2-hydroxyethyl)-2,3-dihydro-6-sulfamoyl-1H-thieno[2,3-b][1,4]thiazine;
3-(2-hydroxyethyl)-2,3-dihydro-4,4-dioxo-6-sulfamoyl-1H-thieno[2,3-b][1,4]thiazine;
methyl (2,3-dihydro-2,4,4-trioxo-6-sulfamoyl-1H-thieno[2,3-b][1,4]thiazin-3-yl)acetate;
methyl (2,3-dihydro-2-oxo-6-sulfamoyl-1H-thieno[2,3-b][1,4]thiazin-3-yl)acetate;
N-isobutyl (2,3-dihydro-2-oxo-6-sulfamoyl-1H-thieno[2,3-b][1,4]thiazin-3-yl)acetamide;
N-methoxyethoxyethyl-N-methoxyethyl-(2,3-dihydro-2,4,4-trioxo-6-sulfamoyl-1H-thieno[2,3-b][1,4]thiazin-3-yl)acetamide;
3-[2-(N-methoxyethoxyethyl-N-methoxyethylamino)ethyl]-2,3-dihydro-2,4,4-trioxo-6-sulfamoyl-1H-thieno[2,3-b][1,4]thiazine;
3-(2-isobutylaminoethyl)-2,3-dihydro-4,4-dioxo-6-sulfamoyl-1H-thieno[2,3-b][1,4]thiazine;
3-[2-bis-(2-methoxyethyl)aminoethyl]-2,3-dihydro-4,4-dioxo-6-sulfamoyl-1H-thieno[2,3-b][1,4]thiazine;
3-[2-(N-methoxyethoxyethyl-N-methoxyethylamino)ethyl[-2,3-dihydro-4,4-dioxo-6-sulfamoyl-1H-thieno[2,3-b]1,4]thiazine;
3-(2-morpholinoethyl)-2,3-dihydro-4,4-dioxo-6-sulfamoyl-1H-thieno[2,3-b][1,4]thiazine;
or an opthalmologically acceptable salt thereof.

* * * * *